United States Patent [19]

Hiji

[11] Patent Number: 4,912,089
[45] Date of Patent: Mar. 27, 1990

[54] CARIOSTATIC MATERIALS AND FOODS, AND METHOD FOR PREVENTING DENTAL CARIES

[76] Inventor: Yasutake Hiji, c/o Tottori University School of Medicine, 86, Nishi-machi, Yonago-shi, Tottori-ken, Japan

[21] Appl. No.: 117,587

[22] Filed: Nov. 6, 1987

[30] Foreign Application Priority Data

Nov. 7, 1986 [JP]  Japan ................................ 61-263867
Feb. 25, 1987 [JP]  Japan ................................ 62-42416

[51] Int. Cl.$^4$ ............................................ A61K 31/70
[52] U.S. Cl. ..................................... 514/25; 514/835; 426/804
[58] Field of Search ............... 424/195.1; 514/25, 835; 426/804

[56] References Cited

U.S. PATENT DOCUMENTS 4,767,286  8/1988  Hiji ................................... 424/195.1

OTHER PUBLICATIONS

Chem. Abst., 79:124843c, 1973.

*Primary Examiner*—John W. Rollins
*Attorney, Agent, or Firm*—Armstrong, Nikaido, Marmelstein, Kubovcik & Murray

[57] ABSTRACT

The decomposition of sugar and production of glucan by Streptococcus mutans which causes dental caries are prevented by a purified Gymnemic acid as a cariostatic material derived from *Gymnema sylvestre*. The *Gymnema sylvestre* itself is used as a cariostatic food.

7 Claims, 3 Drawing Sheets

CARIOSTATIC MATERIALS AND FOODS, AND METHOD FOR PREVENTING DENTAL CARIES

BACKGROUND OF THE INVENTION

1. Field of the Invention

The present invention relates to cariostatic materials and foods and further to a method for preventing dental caries.

2. Description of the Prior Art

Dental caries afflict humankind from ancient times, and particular attention has been given to a relationship between sugar and dental caries from the time when it was prevailingly said that "Degree of Consumption of Sugar is Barometer of Culture". Many results of researchers for prevention of dental caries have been accumulated.

Basic points of view of methods for preventing dental caries have conventionally been in that Streptococcus mutans which are one kind of Streptcoccus are excluded from the mouth or oral cavity by administration of germicide or antibiotic; in that cariostatic artificial sweet materials are employed and sugar is not ingested; and in that dentine is strengthened using fluoridating to resist the attack by the Streptoccocus mutans.

However, it has recently been proposed that dental caries start with decomposition of sugar present in the mouth by the Streptococcus mutans to produce a highly sticky glucan (polysaccharide) which is then adhered to surfaces of teeth to form bacterial plaque. Now, it is an established theory in the academic world that the formation of such plaque is the cause for growing up of dental caries.

In view of this, if, in addition to the above caries preventing methods, the formation of plaque on tooth surfaces will be inhibited by preventing production of glucan, the growing up of dental caries can be avoided reliably.

Thereupon, many researchers have made zealous efforts on studies in search of cariostatic materials, but at present, no effective cariostatic material has been found.

SUMMARY OF THE INVENTION

With the foregoing in view, it is an object of the present invention to provide cariostatic materials and foods and further a method for preventing dental caries, wherein a remarkable plaque formation inhibitory effect can be attained.

To accomplish the above object, the present inventor has found as a result of repeated researches that a plant, *Gymnema sylvestre*, which belongs to the family of Asclepiadaceae and grows naturally in India, Africa and China, has a cariostatic property of inhibiting the production of the above-described glucan thereby to prevent the plaque formation on the tooth surfaces.

A purified Gymnemic acid derived from the aforesaid *Gymnema sylvestre* particularly exhibits a significant cariostatic property.

A tea produced by subjecting dried leaves of *Gymnema sylvestre* to a roasting treatment also has a cariostatic effect of inhibiting generation of an insoluble glucan which would cause dental caries by the Streptococcus mutans.

Incidentally, Gymnemic acid has an effect of inhibiting the absorption of sucrose and the like through the intestinal tract when it is employed in low-caloric foods and beverages. This has already been proposed in U.S. patent application Ser. No. 745,161 now abandoned and its Continuation Application Ser. No. 8,081 now U.S. Pat. No. 4,761,286 by the present applicant. Gymnemic acid is non-toxic to a human body.

Examples evidencing the effect exhibited by cariostatic materials and foods according to the invention will be described in conjunction with the accompanying drawings.

DESCRIPTION OF THE PREFERRED EMBODIMENTS

[Extraction and Purification of Gymnemic Acid]

Figure 1:
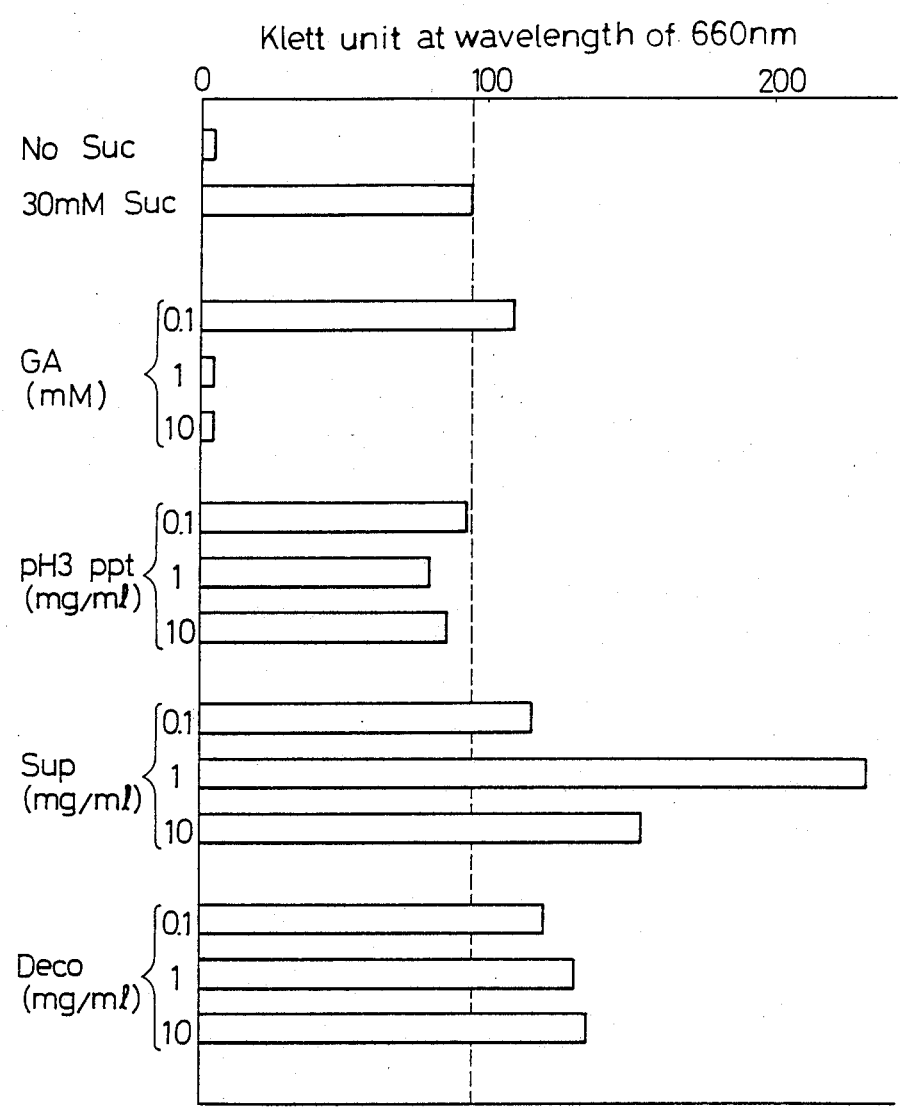
FIG. 1 is a graph illustrating Klett units obtainable at a wavelength of 660 nm, which represent the degree of formation of plaque in various liquid culture media.

To achieve purified Gymnemic acid, 200 g of dried leaves of *Gymnema sylvestre* are first immersed in a warm water at 60° C. for about 5 hours, and this operation is repeated four or five times to provide a warm water-extraction solution containing crude Gymnemic acid. If this extraction is effected using an alcohol from the beginning, chlorophyll, lipid and the like are eluted. Hence, warm water is used in my extraction process to avoid this.

The warm water-extraction solution is adjusted into pH of 3 with a 2N solution of sulfuric acid to give a precipitate containing crude Gymnemic acid.

The precipitate is collected by a centrifugal sedimentation at 15,000 rpm for 15 minutes, and the collected material is washed with water and then extracted 4 or 5 times with ethanol to give an ethanol-extraction solution. This ethanol extraction is carried out for the purpose of removing protein, polysaccharide and the like from the precipitate.

The ethanol-extraction solution is concentrated under a reduced pressure, and acetone is added to the resulting concentrate in an amount two times that of the latter in volume, followed by a centrifugal sedimentation.

The supernatant fluid containing crude Gymnemic acid obtained after the sedimentation is concentrated and dried up under a reduced pressure, and extraction of the dried up material is repeated several times at a boiling point by adding diethyl carbonate as a solvent thereto.

The precipitate from the solvent is collected and then evaporated for dry, and the resulting material is subjected to a fast liquid chromatography. A large-sized column is filled with a reversed phase carrier ($C_{18}$), and a gradual elution is effected so that a mobile phase is converted from a proportion of water to methanol of 1:1 to a proportion of methanol of 100%. As a result, purified Gymnemic acid is eluted in a phase having a methanol concentration of 60 to 70%. The eluted liquid is evaporated for dry and adjusted into pH of 7 to give the Gymnemic acid in the form of Na, K or $NH_4$ salt.

This purified Gymnemic acid is a saponin of one kind (glycoside). The yield of the purified Gymnemic acid is of 0.1 to 0.5% by weight per 100 g of the dried leaves of *Gymnema sylvestre*.

ASSAY EXAMPLE I

Selected specimens were a warm water-extracted material, a precipitate at pH of 3, a supernatant fluid at pH of 3 and a purified Gymnemic acid obtained in each step of the above described extracting process. For the warm water-extracted material, the precipitate and the supernatant fluid, solutions having concentrations of 0.1, 1 and 10 mg/ml were prepared. And in the case of the purified Gymnemic acid, solutions with concentrations of 0.1, 1 and 10 mM were prepared.

Prepared culture media (TTY basic culture media) were a culture medium free of sucrose, a culture medium containing 30 mM of sucrose and culture media produced by individually incorporating 30 mM of sucrose into the afore-mentioned solutions. Streptococcus mutans, II D 973 strain were implanted at 100 μl/4 ml into each of liquid media and subjected to a test tube culture at 37° C. for 48 hours.

In each of the liquid media, the degree of formation of plaque caused by the produced glucan was determined by pulverizing the plaque and then measuring the pulverized plaque for Klett unit by use of a turbidity meter with a wavelength of 660 nm.

FIG. 1 shows the results of this determination. In the liquid medium (No Suc) free of sucrose, the formation of glucan and thus of plaque was not observed, and the measured value was not more than 2 Klett unit, whereas about 100 Klett unit was measured in the liquid medium (30 mM Suc) containing 30 mM of sucrose.

In the liquid medium (GA) containing of 30 mM of sucrose and the purified Gymnemic acid, the measured value, when the purified Gymnemic acid was contained in an amount not less than 1 mM, was of 2 Klett unit similar to that in the aforesaid case of No Suc medium and hence, the formation of plaque was inhibited. However, with a content of the purified Gymnemic acid not more than 0.1 mM, such plaque formation inhibiting effect could not be provided.

In the liquid medium (pH 3 ppt) containing 30 mM of sucrose and the precipitate at pH of 3, such plaque formation inhibiting effect could not be provided at the individual concentrations.

On the other hand, a plaque formation promoting effect was revealed in the liquid medium (Sup) containing 30 mM of sucrose and the supernatant at pH of 3 as well as in the liquid medium (Deco) containing 30 mM of sucrose and the warm water solution.

As apparent from the above results, it is desirable to contain 1 mM or more of a purified Gymnemic acid for the purpose of inhibiting the formation of plaque. In addition, it is an essential requirement to sufficiently purify a Gymnemic acid, because the plaque formation promoting effect was revealed with the aforesaid Sup and Deco media containing the crude Gymnemic acid.

ASSAY EXAMPLE II

The same Streptococcus mutans as in Assay Example I were implanted in a liquid medium (TTY basic medium) containing 56 mM of glucose, and a purified Gymnemic acid was added thereto at various concentrations. The resulting materials were subjected to a test tube culture at 37° C. for 48 hours and examined for presence and absence of an effect of arresting the growth of the Streptococcus mutans. The number of Streptococcus mutans was determined by measuring Klett unit by use of a densitometer at a wave length of 660 nm. At the time of implanting, the number of Streptococcus mutans was of 10 Klett unit.

After the test tube culture, the number of Streptococcus mutans was of 100 Klett unit with the liquid medium free of the purified Gymnemic acid, but was extremely decreased to 40 Klett unit with the liquid medium containing 10 mM of the purified Gymnemic acid added therein. However, with the added amount of purified Gymnemic acid of 1 mM, the number of Streptococcus mutans was less decreased and was of 80 Klett unit.

In addition, it was confirmed that the Streptococcus mutans could not be propagated unless glucose was present, and the number of Streptococcus mutans as implanted in the liquid medium free of glucose did not vary from that at the time of implanting and was of 10 Klett unit.

Further, it was also confirmed that even if the Streptococcus mutans were propagated in the presence of glucose, no glucan was produced and thus, no plaque was formed, unless sucrose was present.

The above results showed that in order to significantly inhibit the growth of the Streptococcus mutans, it is necessary to contain 10 mM or more of the purified Gymnemic acid.

Therefore, it is apparent from Assay Examples I and II that to prevent the formation of plaque and to inhibit the growth of the Streptococcus mutans, it is desirable to contain 10 mM or more of the purified Gymnemic acid. Specific examples of such applications include tooth powders, chewing gums, sugar and the like, which contain purified Gymnemic acid. Such purified Gymnemic acid can be used alone as a preventive.

[Production of Tea]

The tea according to the present invention can be produced through the following steps.

These steps include an air drying step of drying fresh leaves of *Gymnema sylvestre* at ambient temperature for 7 days into a dried up condition, and a roasting step of placing the dried-up leaves into a roaster to roast them at 200° to 300° C. for 15 minutes while rotating the roaster.

Therefore, the tea according to the present invention belongs to a coarse tea type in the classification of processes for producing Japanese tea and has a dark brown color.

For comparison, the aforesaid leaves are used to produce teas of a green tea type, a half-fermented tea type and a full-fermented tea type.

The green tea may be produced through the following steps and its color is green.

These steps include a steaming step of steaming the fresh leaves until a grassy smell disappears and then cooling them, a dehumidification step of swishing water off from the steamed leaves while loosening the latter to facilitate rumpling of the leaves, a rotation-rumpling step of rumping the leaves with a sufficient force applied thereto to destroy the tissue and cells of the leaves for softening thereof, a step of loosening lumps of the leaves at a final stage of the rotation-rumpling step, a middle-rumpling of rumpling up the leaves while drying them so that the leaves may be twisted (in this step, the leaves get polish and diffuse a perfume or aroma), a finish-rumpling step of adjusting the shapes of leaves and improving the flavor of the leaves, and a step of drying the leaves at about 90° C. for about 30 minutes.

The half-fermented tea may be produced through the following steps and has a dark green color.

These steps include a sunlight withering step of subjecting the above-described fresh leaves to sunlight for 2 to 3 hours with stirring them reversed after every lapse of 20 to 30 minutes and activating the evaporation of water and enhancing the activity of enzyme to accelerate the fermentation, a room withering step of stirring the stationary-left leaves after every lapse of one hour and continuing such stirring for 5 to 7 hours to bring about a fermented condition which is inherent to half-fermented tea, a kiln treating step of subjecting the leaves to a high temperature to suppress the activity of enzyme and rapidly evaporating water to soften the tissue into a condition suitable for the subsequent rumpling, a rumpling step of leaving the leaves to stand for 20 minutes and then rumpling such leaves for 10 minutes to loosen them, and a step of drying the leaves at about 90° C. for about 30 minutes.

The full-fermented type tea may be produced through the following steps and has a dark green color.

These steps include a withering step of spreading over the above-described fresh leaves into a thin layer in a room to wither them, thereby facilitating the subsequent rumpling and twisting, a rumpling and twisting step of subjecting the leaves to a sufficient twisting to squeeze the sap from the leaves, thereby destroying the tissue and cells, so that the fermentation is well accelerated, a step of loosening the leaves in the form of lumps by dashing and then screening or sifting the leaves in order to provide a uniform fermentation, a fermentation step of bringing the fermentation already proceeding from the withering stage into a final fermentation stage (the flavor of the full-fermented type tea depends upon this step), and a drying step of evaporating water in the leaves into a level near to a content of 5% to stop the fermentation and then drying them.

The yield of each of the above-described teas is of about 12% based on the weight of the fresh leaves of *Gymnema sylvestre*.

Two grams of each of the aforesaid teas was immersed in 500 ml of hot water at about 80° C. for 3 minutes to make a tea drink. The resulting tea drinks were measured for their optical densities by use of a spectrophotometer to determine the color. The results are given in Table 1.

TABLE I

| Type of tea | Wave length (nm) | | | | | | Color of tea drink |
| | 440 (Purple) | 450 (Blue) | 520 (Green) | 570 (Yellow) | 620 (Orange) | 660 (Red) | |
|---|---|---|---|---|---|---|---|
| The present invention (Coarse tea) | 0.97 | 0.36 | 0.15 | 0.09 | 0.06 | 0.04 | Light red brown |
| Green tea | 0.68 | 0.12 | 0.04 | 0.04 | 0.03 | 0.03 | Yellowish green |
| Half-fermented tea | 0.75 | 0.18 | 0.07 | 0.05 | 0.03 | 0.03 | Yellowish brown |
| Full-fermented tea | 1.15 | 0.26 | 0.10 | 0.08 | 0.05 | 0.04 | Yellowish brown, Slightly clouded |

It can be seen from Table 1 that the optical density is in a larger range of from 440 nm (purple) to near 520 nm (green) is the case of the coarse tea drink according to the present invention and hence, the color of such tea drink is brown near to red. In addition, with the green tea drink, the optical density up to 450 nm (blue) is relatively large and hence, the color of the green tea drink is yellowish green, while the colors of the half-fermented tea drink and the full-fermented tea drink are yellowish brown between the colors of the coarse tea drink and the green tea drink. In this case, it is believed that the reason why the optical density in the full-fermented tea drink is particularly larger in a region of shorter wavelength is because of clouding produced following the fermentation.

A functional test was carried out at a temperature of 60° C. for individual type tea drinks achieved in the above-described manner, of which results are given in Table II. Panels were four men of 27 to 45 years old, and instructions were given to them to represent the strength of taste (bitterness, sweetness and astringency), the levels of smell and color, and the entire valuation in terms of 5-rank integers. The average values are shown in Table II. In the 5-rank representation, "very good" (or "very strong") is represented by 5; "good" (or "strong") is by 4; "mean" is by 3; "bad" (or "weak") is by 2; and "very bad" (or "very weak") is by 1.

TABLE II

| Type of tea | Strength of taste | | | level | | Entire valuation | Note |
| | bitterness | sweetness | astringency | smell | color | | |
|---|---|---|---|---|---|---|---|
| Present Invention (Coarse tea) | 2.75 | 2.75 | 3.25 | 4.00 | 4.00 | 4.00 | Nice-smelling, easy to drink |
| Green tea | 2.75 | 3.50 | 3.00 | 3.00 | 4.67 | 3.25 | Grassy-smell, strange taste |
| Half-fermented tea | 4.50 | 3.00 | 4.75 | 2.00 | 3.00 | 1.25 | Bad-taste, strong bitterness |
| Full-fermented tea | 3.33 | 3.33 | 4.00 | 1.33 | 1.67 | 1.33 | Putrid odor, feel nausea |

It can be seen from Table II that the coarse tea drink according to the present invention is at a mean level for the strength of taste, i.e., the bitterness, the sweetness and the astringency, but is favorable for the levels of smell and color and highest for the entire valuation.

The green tea drink indicates a higher value in sweetness of the strength of taste, but is at mean level all over. Its color of clear yellowish green gives a good impression, but the entire valuation is lower than that of the coarse tea drink, because grassy-smell was partially commented.

The half-fermented tea drink is lower in the entire valuation because of strong bitterness and astringency commented, and the full-fermented tea drink is likewise extremely low in the entire valuation because the smell is near a putrid odor and the tea drink is slightly cloudy.

ASSAY EXAMPLE III

Extracts were derived respectively from the above-described type individual teas in the following procedure.

Five grams of each tea was immersed in 1,000 ml of hot water at 90° C. for 10 minutes to produce a tea drink. This step was repeated twice by using the same tea leaves and tea drinks obtained by the first and second steps were mixed together, and the resulting mixture was concentrated in an evaporator and then subjected to a freeze-drying to provide an extract. The yield was of about 25%.

Figure 2B:
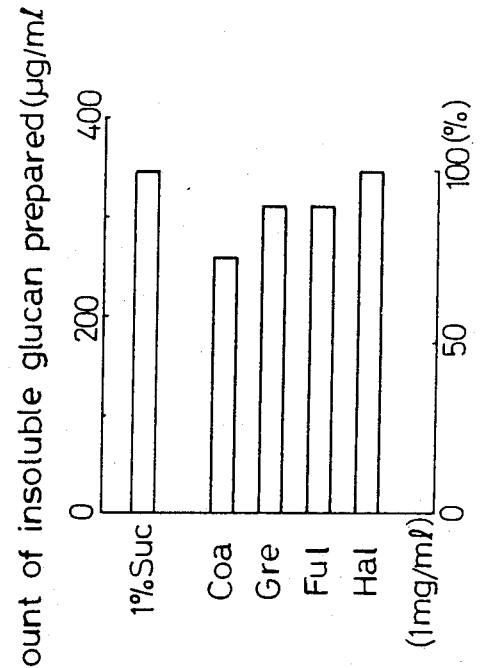
FIGS. 2A and 2B are graphs illustrating values of amount of insoluble glucan prepared in mixture of extracts from various types of tea drinks produced from Gymnema sylvestre and sucrose solution, as measured after lapse of a predetermined time, respectively.
Figure 2A:
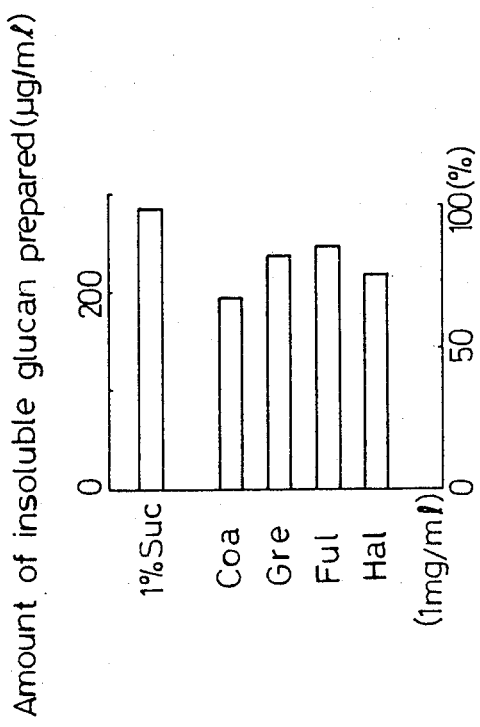

Each of such extracts was added into a 1% solution of sucrose so that the concentration thereof was of 1 mg/ml, and Streptococcus mutans were implanted to observe the sequence of preparation of an insoluble glucan. The prepared insoluble glucan was subjected to a centrifugal sedimentation and then its amount was measured in an anthrone sulfuric acid process to provide the results given in FIGS. 2A and 2B. FIG. 2A illustrates the results provided after lapse of 12 hours, and FIG. 2B illustrates the results provided after lapse of 18 hours. In these Figures, Coa indicates the results when the extract from the coarse tea according to the present invention was added, and Gre, Ful and Hal indicate the results when extracts from the green and full-fermented and half-fermented teas were added, respectively. 1% Suc indicates the results with only sucrose.

It is apparent from FIG. 2 that if the extract from the coarse tea according to the present invention is added, the preparation of an insoluble glucan is inhibited.

The tea drink produced from the above method is substantially the same in taste as the commercially available common green teas and moreover, is nice-smelling and easy to drink and thus satisfies requirements for beverages.

Figure 3:
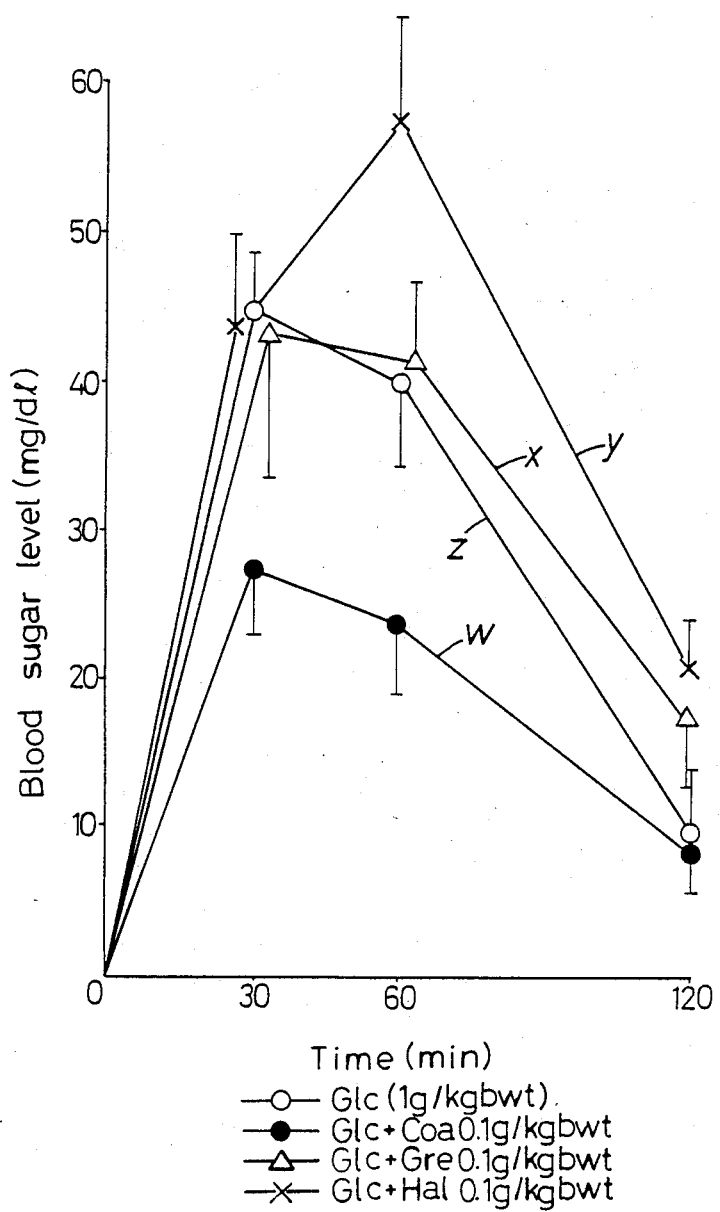
FIG. 3 is a graph illustrating a relationship between time and blood sugar content induced by intake of both of extracts from various tea drinks produced from *Gymnema sylvestre* and a solution of glucose.

FIG. 3 illustrates an effect of inhibiting increase in the blood sugar content by an extract from the coarse tea according to the present invention in comparison with that provided by the other type teas. Namely, FIG. 3 illustrates the results obtained from an oral glucose tolerance test in which wister strain normal male rats (weighing 350 to 450 g) were used to examine increase in the blood sugar content (blood plasma level) from the time of an empty stomach. Dosage of glucose was 1 g per kg body weight of the rat, and the amount of each extract added was of 0.1 g per kg body weight, corresponding to one tenth of the amount of glucose. The number of cases in this test was of 10 to 27, and the blood sugar content at the time of an empty stomach was of $90.0 \pm 2.6$ mg/dl (mean$\pm$S.E and so in the following, n=27).

In FIG. 3, lines w, x and y indicate the results obtained from the addition of the individual extracts from the coarse tea according to the present invention and the green tea and half-fermented tea in the comparative examples, and a line z indicates the results obtained from the administration of only glucose.

It is apparent from FIG. 3 that the rise in the blood sugar content is substantially inhibited are indicated by the line w when the extract from the coarse tea according to the present invention was added. For example, when only glucose was administered, an increase in blood sugar content to $44.7 \pm 4.0$ mg/dl was exhibited in 30 minutes after administration, whereas when the extract from the coarse tea was added, the blood sugar content was decreased to $27.1 \pm 4.4$ mg/dl.

When the extracts from the green tea and the half-fermented tea were added, the tendency to accelerate the increasing of the blood sugar content was observed. This was similar with the extract from the full-fermented tea.

The similar test using 2 g/kg body weight of sucrose in place of glucose showed that rise of the blood sugar content could be inhibited by addition of the extract from the coarse tea according to the present invention. For example, when only sucrose was administered, an increase in blood sugar content to $44.1 \pm 5.1$ mg/dl was exhibited in 30 minutes after administration, whereas when the extract from the coarse tea was added, the blood sugar content was decreased to $32.9 \pm 5.8$ mg/dl.

What is claimed is:

1. A method for preventing dental caries which comprises adding a cariostatically effective amount of Gymnemic acid to a food stuff and at least contacting teeth with the foodstuff.

2. The method of claim 1 wherein said Gymnemic acid is derived from *Gymnema sylvestre*.

3. The method of claim 1 wherein said foodstuff is sugar.

4. The method of claim 3 wherein said sugar is sucrose.

5. The method of claim 3 wherein said sugar is glucose.

6. The method of claim 3 wherein Gymnemic acid is added in amounts of 10 mM or more to the sugar.

7. The method of claim 2 wherein *Gymnema sylvestre* leaves are dried and roasted.

* * * * *

UNITED STATES PATENT AND TRADEMARK OFFICE
CERTIFICATE OF CORRECTION

PATENT NO. : 4,912,089
DATED : March 27, 1990
INVENTOR(S) : Yasutake HIJI

It is certified that error appears in the above-identified patent and that said Letters Patent is hereby corrected as shown below:

On the cover page, Item [56], "4,767,286" should read

--4,761,286--.

Signed and Sealed this

Thirtieth Day of July, 1991

Attest:

HARRY F. MANBECK, JR.

*Attesting Officer*      *Commissioner of Patents and Trademarks*